(12) United States Patent
Tiu

(10) Patent No.: US 6,482,174 B2
(45) Date of Patent: Nov. 19, 2002

(54) SYRINGE HAVING NEEDLE SAFELY RECEIVING STRUCTURE

(76) Inventor: Bruce Tiu, 22/1 Sukhumvit soi 47, Wattana Bangkok 10110 (TH)

( * ) Notice: Subject to any disclaimer, the term of this patent is extended or adjusted under 35 U.S.C. 154(b) by 0 days.

(21) Appl. No.: 09/839,085

(22) Filed: Apr. 23, 2001

(65) Prior Publication Data

US 2002/0156396 A1 Oct. 24, 2002

(51) Int. Cl.[7] ................................................ A61M 5/50
(52) U.S. Cl. ...................................... 604/110; 604/195
(58) Field of Search ................................ 604/110, 195, 604/198

(56) References Cited

U.S. PATENT DOCUMENTS

| | | | |
|---|---|---|---|
| 5,785,687 A | * | 7/1998 | Saito .......................... 604/110 |
| 5,951,491 A | | 9/1999 | Wu ............................. 600/576 |
| 6,093,171 A | * | 7/2000 | Huang ......................... 604/110 |
| 6,196,997 B1 | * | 3/2001 | Saito .......................... 604/110 |
| 6,368,306 B1 | * | 4/2002 | Koska .......................... 604/218 |

* cited by examiner

Primary Examiner—Gerald A. Michalsky
(74) Attorney, Agent, or Firm—Charles E. Baxley

(57) ABSTRACT

A syringe includes a nozzle received in a front portion of a barrel, a needle attached to the nozzle, a stem having a piston slidably received in the barrel and movable toward and away from the nozzle. The piston has a latch for latching to the nozzle and to move the nozzle and the needle inward of the barrel after use. One or more coupling members are coupled between the stem and the piston for allowing the stem to be bent and disengaged from the piston. The piston includes one or more catches for retaining the piston in the barrel after the piston is moved inward of the barrel.

1 Claim, 5 Drawing Sheets

SYRINGE HAVING NEEDLE SAFELY RECEIVING STRUCTURE

BACKGROUND OF THE INVENTION

1. Field of the Invention

The present invention relates to a syringe, and more particularly to a syringe including a needle safely receiving structure for safely receiving the needle after use and for preventing the syringe from being used again after use.

2. Description of the Prior Art

Typical syringes may be used to draw blood, or may be used to inject medicine into human bodies. Due to the acquired immune deficiency syndrome (AIDS) and the other contagious diseases, the needles of the syringes, and even the syringes themselves, should not be used again and should be discarded right after use, for safety purposes.

U.S. Pat. No. 5,951,491 to Wu discloses one of the typical syringes including a piston rod that may be broken and disengaged from the piston after use. However, the needle may not be safely received in the syringe housing and may also be exposed and may also be contacted or hurt the other people inadvertently after use. The typical syringes may be used again after the first use.

The present invention has arisen to mitigate and/or obviate the afore-described disadvantages of the conventional syringes.

SUMMARY OF THE INVENTION

The primary objective of the present invention is to provide a syringe including a needle safely receiving structure for safely receiving the needle after use and for preventing the syringe from being used again after use.

In accordance with one aspect of the invention, there is provided a syringe comprising a barrel including a front portion and a rear portion, a nozzle received in the front portion of the barrel and including a front portion, a needle attached to the front portion of the nozzle and extended outward of the barrel, a stem including a piston slidably received in the barrel and movable toward and away from the nozzle, and the piston including latch means for latching to the nozzle and to move the nozzle inward of the barrel after the latch means has been engaged into the nozzle. The nozzle and thus the needle may be pulled inward of the barrel after use, such that the nozzle and the needle may be prevented from being used again after use.

The barrel includes means for preventing the nozzle from being moving outward through the front portion of the barrel. The preventing means includes a peripheral shoulder formed in the front portion of the barrel for engaging with the nozzle and for preventing the nozzle from being moving outward through the front portion of the barrel.

The barrel includes means for detachably securing the nozzle to the barrel. The detachably securing means includes a peripheral rib formed in the front portion of the barrel, the nozzle includes an outer peripheral recess formed therein for receiving the peripheral rib of the barrel and for detachably securing the nozzle to the barrel.

The nozzle includes a chamber formed therein, the latch means of the piston includes a latch extended from the piston for engaging into the chamber of the nozzle.

The nozzle includes means for retaining the latch in the chamber of the nozzle. The latch includes an orifice formed therein for increasing a deformability of the latch.

The nozzle includes at least one groove formed therein for defining at least one spring blade therein and for facilitating an engagement of the latch into the chamber of the nozzle.

The stem includes means for detachably securing the stem to the piston. The detachably securing means of the stem includes at least one coupling member coupled between the stem and the piston for allowing the stem to be disengaged from the piston when the stem is bent relative to the piston.

The detachably securing means of the stem includes an extension extended from the piston, and at least one coupling member coupled between the stem and the extension for allowing the stem to be disengaged from the extension when the stem is bent relative to the extension.

The extension includes an enlarged head provided thereon, the detachably securing means of the stem includes at least one coupling member coupled between the stem and the enlarged head for allowing the stem to be disengaged from the enlarged head when the stem is bent relative to the enlarged head.

A device is further provided for preventing the piston from being moving outward and disengaged from the rear portion of the barrel and includes at least one catch extended from the piston for engaging with the barrel and for preventing the piston from being moving outward and disengaged from the rear portion of the barrel.

The piston includes at least one spring leg extended therefrom for supporting the catch. The barrel includes a peripheral flange extended inward of the rear portion thereof for engaging with the catch and for preventing the piston from being moving outward and disengaged from the rear portion of the barrel.

Further objectives and advantages of the present invention will become apparent from a careful reading of a detailed description provided hereinbelow, with appropriate reference to accompanying drawings.

DETAILED DESCRIPTION OF THE PREFERRED EMBODIMENT

Figure 1:
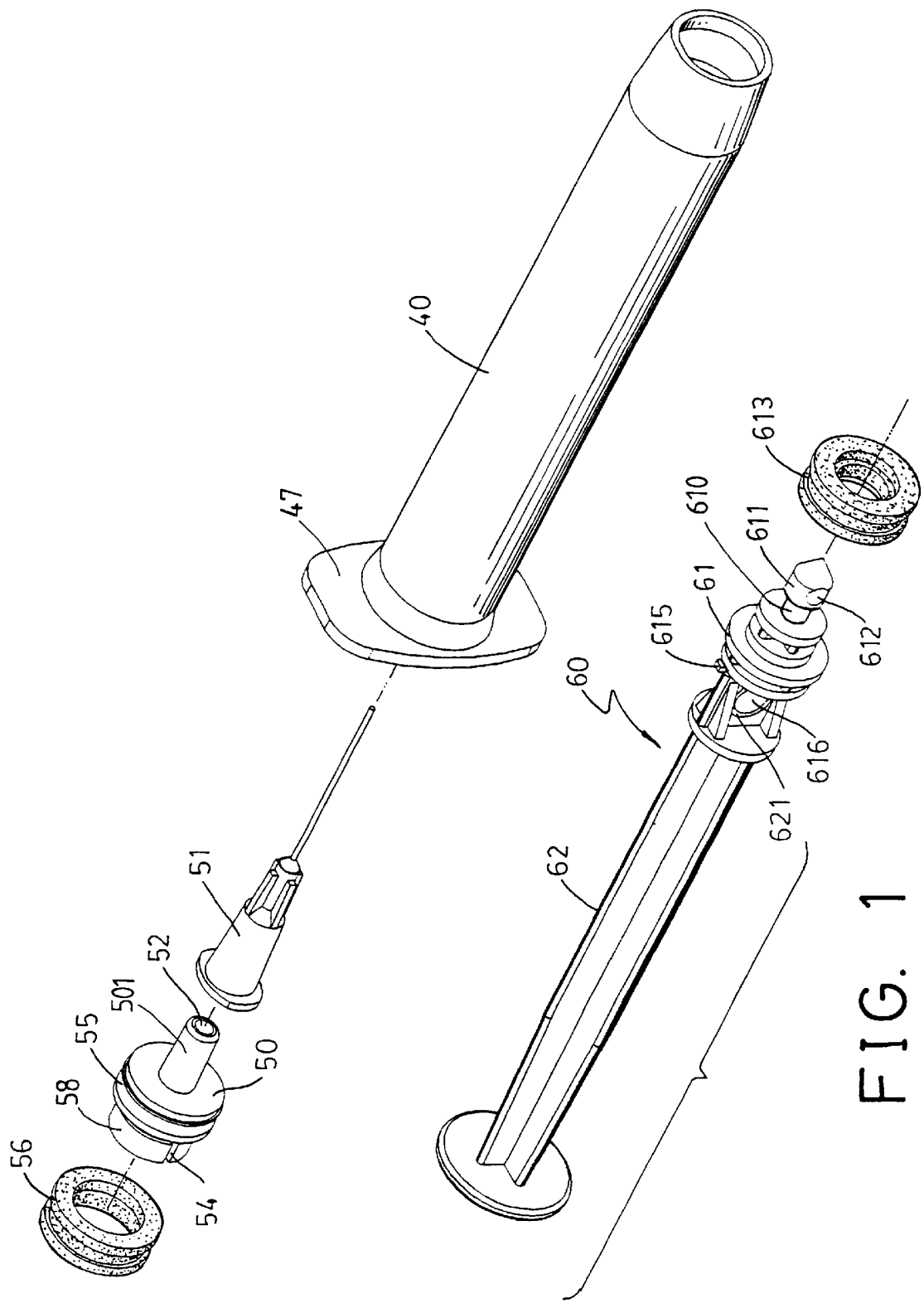
FIG. 1 is an exploded view of a syringe in accordance with the present invention.
Figures 2, 3:
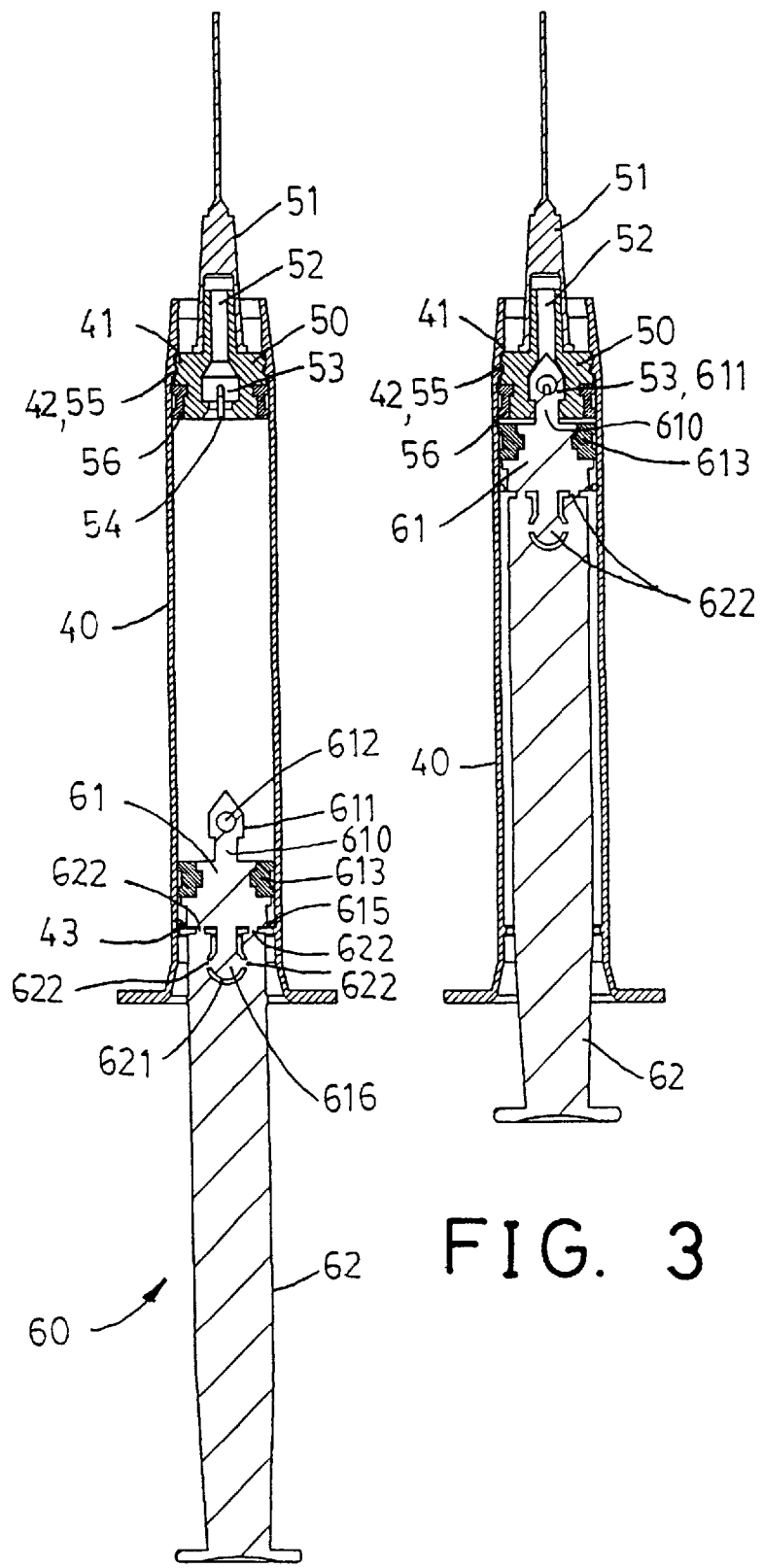
FIGS. 2, 3, 4, 5 are cross sectional views illustrating the operation of the syringe.
Figures 4, 5:
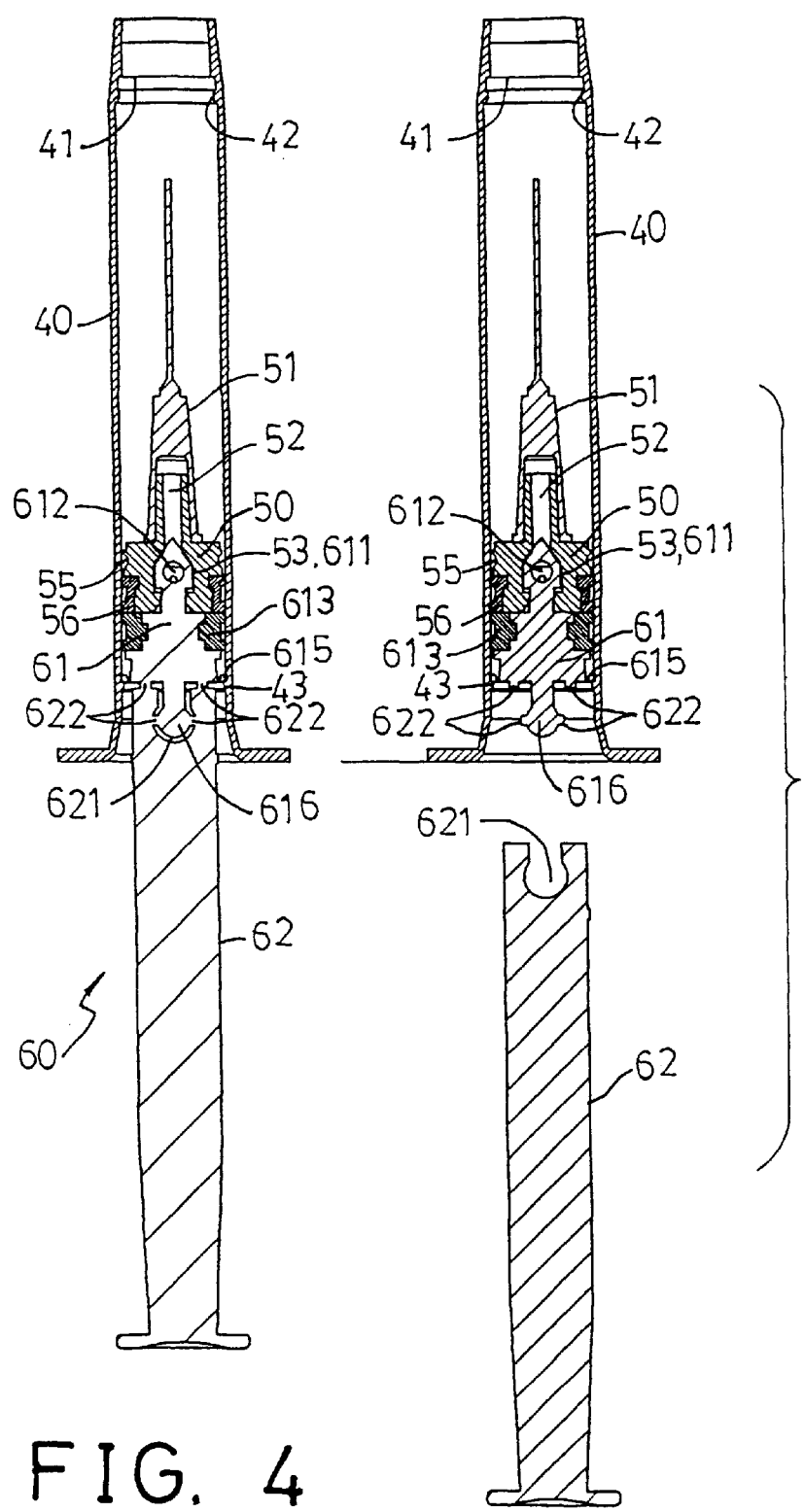

Referring to the drawings, and initially to FIGS. 1 and 2, a syringe in accordance with the present invention comprises a barrel 40 for receiving the blood to be drawn from the patient or for receiving the medicine to be injected into the patient, and including an inner peripheral shoulder 41 and an inner peripheral rib 42 formed in the front portion thereof (FIGS. 2–6) and including an inner peripheral flange 43 formed in the rear portion thereof (FIGS. 7, 8) and including an enlarged panel 47 extended laterally outward from the rear portion thereof for being held or grasped by the users.

A nozzle 50 is engaged in the front portion of the barrel 40 and includes a peripheral recess 55 formed in the outer peripheral portion thereof for receiving the peripheral rib 42 of the barrel 40 and for detachably securing the nozzle 50 in the front portion of the barrel 40, and for allowing peripheral rib 42 of the barrel 40 to be disengaged from the peripheral recess 55 of the nozzle 50 and for allowing the nozzle 50 to be engaged into the barrel 40 (FIGS. 4, 5) after use. The nozzle 50 may be engaged with the peripheral shoulder 41 of the barrel 40 for preventing the nozzle 50 from being moved out and disengaged from the barrel 40.

The nozzle 50 includes a tube 501 extended forward therefrom for attaching or securing a needle 51 thereto, and includes a bore 52 formed therein, and includes a chamber 53 (FIG. 6) formed in the rear portion thereof and communicating with the bore 52 thereof, and includes a peripheral bulge 57 extended inward of the chamber 53 of the nozzle 50. The needle 51 is extended outward of the barrel 40 for engaging into human bodies or the like. The nozzle 50 includes one or more grooves 54 formed in the rear portion thereof and communicating with the chamber 53 of the nozzle 50 for forming or defining one or more blades 58 and for increasing the resilience of the rear portion of the nozzle 50 or of the blades 58. A sealing ring 56 is engaged on the rear portion or the blades 58 of the nozzle 50 and engaged between the nozzle 50 and the barrel 40 for making a water tight seal between the nozzle 50 and the barrel 40.

A plunger 60 includes a stem 62 having a front portion slidably engaged and received in the barrel 40, and includes a block or piston 61 attached to the front portion of the stem 62 and slidably engaged in the barrel 40. A sealing ring 613 is engaged between the piston 61 and the barrel 40 for making a water tight seal between the piston 61 and the barrel 40. The plunger 60 includes a rod 610 extended forward of the piston 61, and includes a latch 611 provided on the front end of the rod 610 of the plunger 60 and having an orifice 612 formed therein for increasing the deformable characteristic of the latch 611 and for allowing the latch 611 to be slightly deformed and engaged into the chamber 53 of the nozzle 50 by moving beyond the peripheral bulge 57 of the nozzle 50, best shown in FIG. 6. The latch 611 includes a width or an outer diameter greater than that of the rod 610 of the piston 61 and may be engaged with the peripheral bulge 57 of the nozzle 50 after the latch 611 is engaged into the chamber 53 of the nozzle 50, such that the latch 611 may be prevented from being disengaged from the nozzle 50 after being engaged into the nozzle 50.

Figure 6:
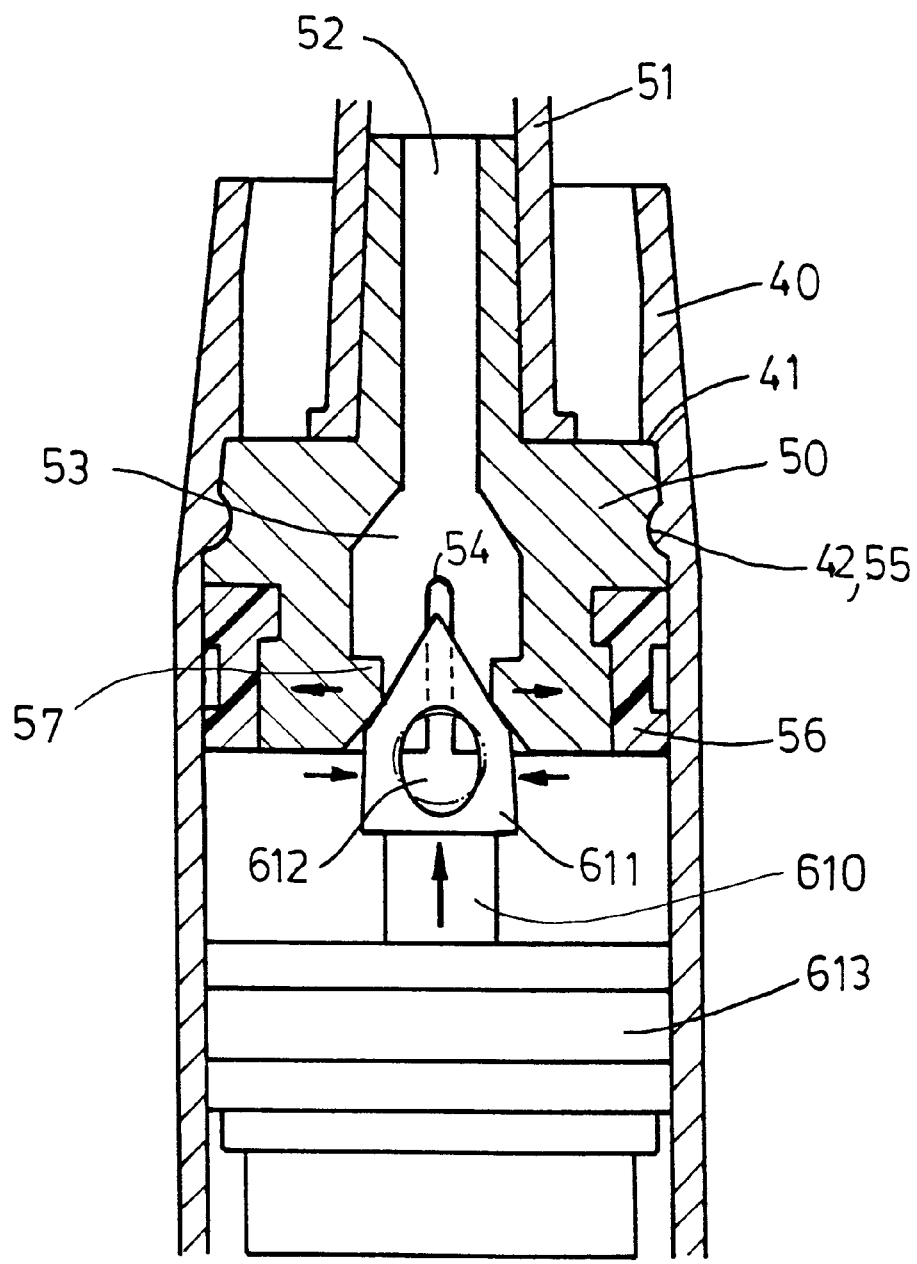
FIGS. 6, 7, 8 are partial cross sectional views illustrating the operation of the syringe.

As shown in FIGS. 3–6, when the medicine received in the barrel 40 has been forced and injected out through the needle 51 by the piston 61 or when the piston 61 is moved and forced toward the nozzle 50, the latch 611 may be forced beyond the peripheral bulge 57 of the nozzle 50 and may be forced into the chamber 53 of the nozzle 50 by the deformable characteristic of the latch 611. The nozzle 50 preferably includes an inclined or tapered peripheral surface formed around the peripheral bulge 57 for engaging with the peripheral inclined or tapered surface of the latch 611 and for allowing the latch 611 to be easily engaged into the chamber 53 of the nozzle 50 and for allowing the blades 58 of the nozzle 50 to be forced to move laterally or radially outward against the sealing ring 56. As best shown in FIG. 6. before the latch 611 is completely engaged into the chamber 53 of the nozzle 50, the orifice 612 of the latch 611 is communicated with the grooves 54 of the nozzle 50, such that the medicine received between the piston 61 and the nozzle 50 may still be forced through the needle 51 via the orifice 612 of the latch 611 and the chamber 53 of the nozzle 50.

Figure 7:
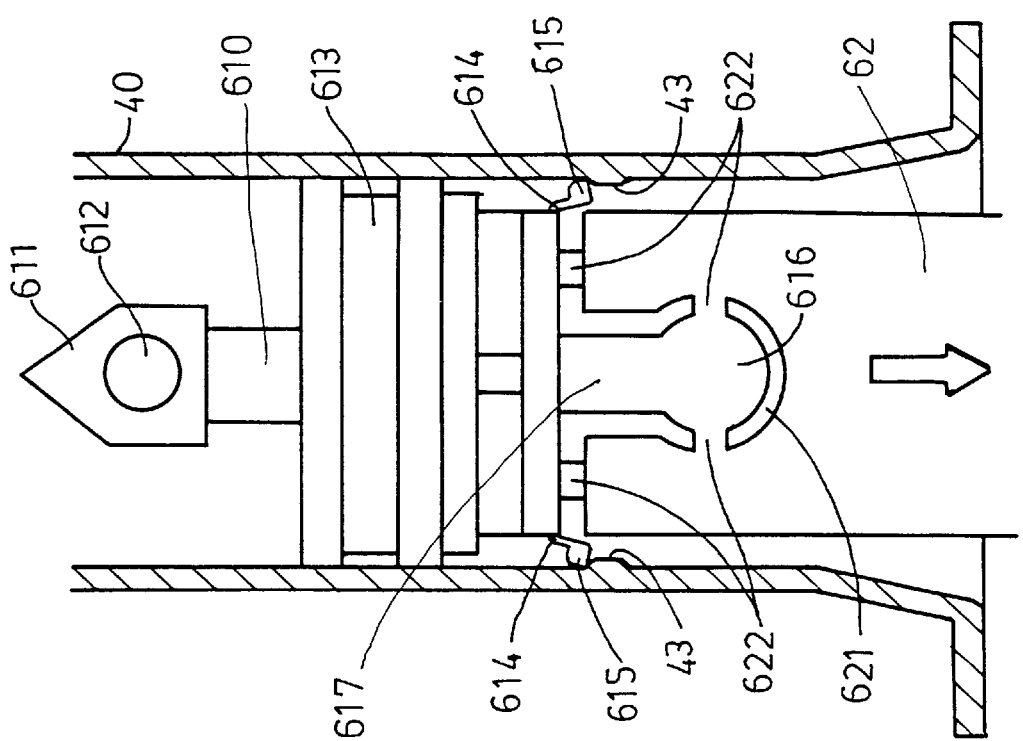
Figure 8:
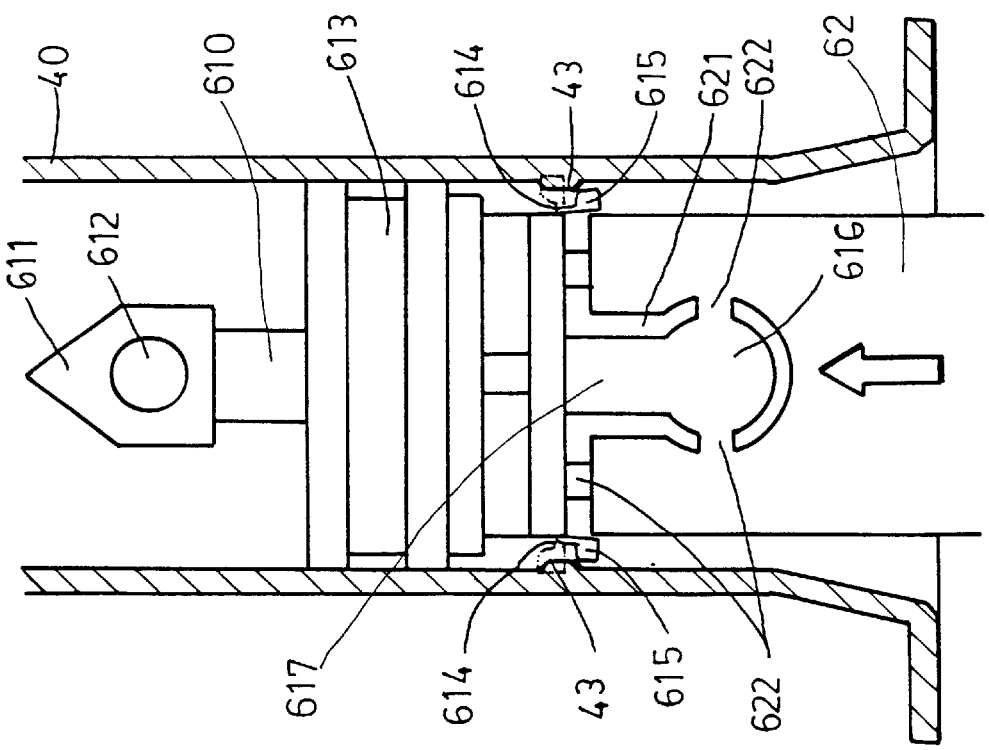

As shown in FIGS. 7, 8, the piston 61 includes an enlarged head 616 formed on the rear portion of an extension 617 that is extended rearward from the piston 61. A gap or a slot 621 is formed between the stem 62 and the piston 61. The stem 62 includes one or more coupling members 622 formed between the stem 62 and the piston 61 and/or the extension 617 or the head 616 of the piston 61, for allowing the stem 62 to be bent or broken or disengaged from the piston 61 (FIG. 5) when the stem 62 is bent relative to the piston 61.

The plunger 60 further includes one or more spring legs 614 (FIGS. 7, 8) extended therefrom and each having a catch 615 provided on the free end of the spring leg 614. The catches 615 may move beyond the peripheral flange 43 of the barrel 40 when the piston 61 is moved toward the nozzle 50, and may be prevented from being moved rearward or backward beyond the peripheral flange 43 of the barrel 40 after the piston 61 has been moved inward of the barrel 40 and has been moved toward the nozzle 50, such that the piston 61 may be prevented from moving outward of the rear portion of the barrel 40 and such that the stem 62 may be bent relative to the piston 61.

In operation, as shown in FIGS. 2 and 3, the medicine received in the barrel 40 may be forced and injected out through the needle 51 by the piston 61 when the piston 61 is moved and forced toward the nozzle 50. The latch 611 may be forced beyond the peripheral bulge 57 of the nozzle 50 and may be forced into the chamber 53 of the nozzle 50 and secured to the nozzle 50. When the stem 62 is pulled rearward, the nozzle 50 and the needle 51 may be pulled inward of the barrel 40 (FIG. 7). The stem 62 may be bent relative to the piston 61 (FIG. 8) such that the nozzle 50 and the needle 51 may be retained in the barrel 40 and may be prevented from being used again after use.

As shown in FIG. 2, when the latch 611 is not engaged into the nozzle 50 yet and when the stem 62 has not been bent relative to the piston 61 and disengaged from the piston 61, the piston 61 may also be used and moved away from the nozzle 50 for drawing the blood or the like into the barrel 40.

Accordingly, the syringe in accordance with the present invention includes a needle safely receiving structure for safely receiving the needle after use and for preventing the syringe from being used again after use.

Although this invention has been described with a certain degree of particularity, it is to be understood that the present disclosure has been made by way of example only and that numerous changes in the detailed construction and the combination and arrangement of parts may be resorted to without departing from the spirit and scope of the invention as hereinafter claimed.

I claim:

1. A syringe comprising:

a barrel including a front portion having a peripheral rib formed therein, and including a rear portion having a peripheral flange extended inward of said rear portion thereof, a nozzle received in said front portion of said barrel, and including an outer peripheral recess formed therein for receiving said peripheral rib of said barrel and for detachably securing said nozzle to said barrel, said nozzle including a chamber formed therein, and including a rear portion having at least one groove formed therein and communicating with said chamber thereof for defining at least one spring blade therein, and including a front portion, a needle attached to said front portion of said nozzle and extended outward of said barrel, a piston slidably received in said barrel and movable toward and away from said nozzle, said piston including a latch extended therefrom for engaging into said chamber of said nozzle, and for moving said nozzle inward of said barrel, said at least one spring blade of said nozzle being provided for facilitating an engagement of said latch into said chamber of said nozzle, and for being engageable with said piston to retain said latch in said chamber of said nozzle, said latch including an orifice formed therein for increasing a deformability of said latch, said piston including a rear portion having an extension extended rearwardly therefrom, said extension including a rear portion having an enlarged head formed therein, a stem including a slot formed between said piston and said stem, and including at least one first coupling member provided between said stem and said piston, and including at least one second coupling member coupled between said stem and said enlarged head of said extension, for allowing said stem to be disengaged from said piston and said enlarged head of said extension when said stem is bent relative to said piston and said enlarged head of said extension, and said piston including at least one spring leg extended therefrom, said at least one spring leg including a free end having at least one catch provided thereon for engaging with said peripheral flange of said barrel and for preventing said piston from being moving outward and disengaged from said rear portion of said barrel.

* * * * *